(12) United States Patent
Töllner

(10) Patent No.: US 6,533,783 B1
(45) Date of Patent: Mar. 18, 2003

(54) CATHETER

(75) Inventor: Thomas Töllner, Berlin (DE)

(73) Assignee: Biotronik Mess -und Therapiegeraete GmbH & Co. Ingenieurbuero Berlin, Berlin (DE)

( * ) Notice: Subject to any disclaimer, the term of this patent is extended or adjusted under 35 U.S.C. 154(b) by 14 days.

(21) Appl. No.: 09/615,015

(22) Filed: Jul. 12, 2000

(30) Foreign Application Priority Data

Jul. 14, 1999 (DE) .......................................... 199 33 278

(51) Int. Cl.[7] .......................... A61B 18/18; A61N 1/00; A61M 31/00
(52) U.S. Cl. ..................... 606/49; 606/41; 604/95.01; 607/122
(58) Field of Search ................ 606/27–50; 607/46–102, 607/105, 115, 116, 122; 600/434, 435, 585; 604/95.01, 95.04

(56) References Cited

U.S. PATENT DOCUMENTS

| | | |
|---|---|---|
| 4,586,923 A | 5/1986 | Gould et al. ................... 604/95 |
| 5,199,950 A | 4/1993 | Schmitt et al. ................ 604/95 |
| 5,254,088 A | 10/1993 | Lundquist et al. ............. 604/95 |
| 5,273,535 A | 12/1993 | Edwards et al. ............... 604/95 |
| 5,328,467 A | 7/1994 | Edwards et al. ............... 604/95 |
| 5,329,923 A | 7/1994 | Lundquist ..................... 128/642 |
| 5,364,351 A | 11/1994 | Heinzelman et al. .......... 604/95 |
| 5,395,327 A | 3/1995 | Lundquist et al. ............. 604/95 |
| 5,465,716 A | 11/1995 | Avitall ......................... 128/642 |
| 5,643,255 A | 7/1997 | Organ .......................... 606/41 |
| 5,656,030 A | 8/1997 | Hunjan et al. ................. 604/95 |

FOREIGN PATENT DOCUMENTS

| | | |
|---|---|---|
| DE | 15 75 701 | 1/1970 |
| DE | 39 20 707 | 1/1991 |
| DE | 44 17 637 | 11/1995 |
| WO | WO 91/11213 | 8/1991 |
| WO | WO 92/00696 | 1/1992 |
| WO | WO 94/26347 | 11/1994 |
| WO | WO 97/01369 | 1/1997 |
| WO | WO 97/29801 | 8/1997 |
| WO | WO 97/42996 | 11/1997 |
| WO | WO 99/42155 | 8/1999 |

Primary Examiner—Linda C. M. Dvorak
Assistant Examiner—Kenneth Schopfer
(74) Attorney, Agent, or Firm—Hahn Loeser + Parks LLP; Stephen L. Grant

(57) ABSTRACT

In order to ensure a simple structure and precise handling in the case of a catheter, in particular a bi- or unidirectionally deflectable ablation catheter, comprising a flexible guide tube (3) which extends from a gripping element (1) and which terminates in a catheter tip (6) for treating or investigating a hollow organ in a body, wherein provided for deflection purposes there is at least one draw wire (13a; 13b) which extends within the flexible guide tube (3) and which is fixed to the tip (6) of the catheter and which is movable by way of a transmission means disposed in the gripping element (1) for converting the rotary movement of a manual control wheel (7) into a longitudinal movement for the draw wire (13a; 13b), it is proposed that provided as the transmission means is a toothed drive pulley (8) which is coupled to the control wheel (7) and which correspondingly engages into the teeth of a toothed belt (9) which is guided over guide means within the gripping element (1) in such a way that the draw wire (13a; 13b) is pullingly longitudinally movable by way of an entrainment member (12a; 12b) fixed to a flank side (11a; 11b) of the toothed belt (9).

20 Claims, 5 Drawing Sheets

CATHETER

BACKGROUND OF THE INVENTION

Catheters as tubular medical instruments serve for investigating or treating hollow organs in the body. Ablation catheters are a special kind of catheter which are equipped with an electrode and which, using high-frequency electromagnetic waves, permit targeted denaturing of tissue in the heart. Electrophysiological therapy of that kind is usually applied for treating cardiac disrhythmia. In order to position the electrode which is mounted in the region in the tip of the catheter in the heart appropriately for the function involved through the primary vein or artery, the catheter is provided with a control or adjusting mechanism, by means of which the region of the tip of the catheter can be deflected from the exterior in a plurality of directions, that is to say it can be pivoted. The catheter can be targetedly positioned manually by appropriate pivotal movement of the tip of the catheter in conjunction with a forward displacement of the guide tube.

A catheter of the general kind set forth is known from U.S. Pat. No. 5,273,535 to Edwards. The catheter essentially comprises a gripping or handle element which goes into a catheter stem from which extends a flexible guide tube which terminates in a catheter tip with integrated electrode. Disposed at the end of the gripping element which is opposite to the catheter stem is an electric line, by way of which the electrode is supplied with electrical energy.

Two draw wires which are secured to the tip of the catheter extend within the flexible guide tube. The draw wires are arranged in such a way that pulling on one draw wire or the other makes it possible to deflect the tip of the catheter in a first direction or in a direction opposite to the first direction. The draw wires do not provide for the transmission of a pressure force. By virtue of deflection of the tip of the catheter and an additional rotary movement of the guide tube by means of the gripping element, the catheter can follow the curved configuration of a hollow organ in the body, without causing damage thereto.

The draw wires are movable alternately in a pulling mode by way of transmission means which are disposed in the gripping element and which are operated manually by a control element. The control element is here in the form of a control wheel. The transmission means convert the rotary movement of the control wheel into the pulling longitudinal movement for the draw wires. The transmission means comprise a shaft which is arranged stationarily and coaxially with respect to the control wheel and against which a respective draw wire bears from each of both sides. The two draw wires are secured to an apex point on the shaft. If now for example a rotary movement in the counterclockwise direction is effected at the control wheel, then the shaft also rotates in the counterclockwise direction and a wire is wound on to the shaft corresponding to the angle of rotation covered, and is thereby pulled. The other draw wire is correspondingly relieved of load. This involves a deflection movement of the tip of the catheter. Deflection in the opposite direction is produced in a similar manner by way of rotation of the control wheel in the clockwise direction. With this structure, the degree of deflection is established by the diameter of the shaft and is really slight by virtue of the structural boundary conditions involved.

The transmission means further include a locking mechanism in the form of a locking screw in order if necessary to hold the deflected catheter tip in position, that is to say, to prevent it from springing back into the straight position.

Other transmission means are known from U.S. Pat. No. 5,254,088, to Lundquist. Thus, a wedge element which is displaceable in orthogonal relationship to the gripping element can be provided as the control element. Displacement of the wedge element causes pulling of a draw wire which is connected to the wedge element by way of a longitudinal groove. A second draw wire can be operated in the same manner by way of a further wedge element. Handling of these control elements however is really complicated and the degree of deflection in that case is severely limited. As a second alternative, proposed as the control element is a rocker-like pivotal lever which is mounted at the center pivotably in the gripping element and which at both sides of the mounting location has two clamping locations for gripping the draw wires. The pivotal lever which projects on both sides beyond the gripping element makes handling of the catheter more difficult and the degree of deflection is also limited by the angle of pivotal movement. Admittedly, an increase in the distance of the wire-clamping locations from the mounting location could increase the degree of deflection in this arrangement; that however also involves the draw wires spreading to a greater degree, so that handling is worsened due to frictional influences. A third proposed alternative makes use of two control wheels which are arranged one behind the other, with associated shafts, on which a respective draw wire can be wound separately to any desired length. That structure admittedly permits a high degree of deflection but handling is really complicated by the two control wheels to be operated.

U.S. Pat. No. 5,364,351 to Heinzelman discloses a catheter whose transmission means include two racks. A draw wire is disposed at the end of each rack. The racks are arranged to face towards each other with their teeth and are guided longitudinally movably within the gripping element. Engaging therebetween is a gear which is connected to a manual control wheel by way of further gears. This structure can permit a high degree of deflection of the tip of the catheter, by alternate rotary movement at the control wheel. The transmission means however comprise a large number of movable individual parts which each have to be supported or guided according to their respective function.

Therefore the object of the present invention is to provide a catheter, in particular an ablation catheter, which is simple in structure and which is in addition precise in terms of handling.

SUMMARY OF THE INVENTION

Based on a catheter as set forth in the classifying portion of claim 1, that object is attained in conjunction with the characterising features thereof. Advantageous developments of the invention are set forth in the following appendant claims.

The invention includes the technical teaching that provided as a transmission means for a catheter is a toothed drive pulley which is coupled to a manual control wheel and which correspondingly comes into engagement with the teeth of a toothed belt which is guided by way of guide means within the gripping element in such a way that at least one draw wire is pullingly longitudinally movable by way of an entrainment member secured to one flank side of the toothed belt. Precisely two draw wires can be arranged at both flank sides of the toothed belt for bidirectional deflection.

The structure according to the invention has the advantage that a high degree of deflection of the tip of the catheter is possible as the degree of deflection is dependent on the length of the flank side, that is to say ultimately the periphery of the toothed belt used. The structural size of the gripping element can in that way be kept relatively small, which is to the advantage of manual operability. Furthermore the structure according to the invention manages with a small number of individual parts, thereby simplifying the structural configuration involved. Precise handling is governed by the configuration of the draw wires, which is effected very substantially straight and centrally in the gripping element, due to the arrangement of the entrainment members. Due to the resulting, only slight degree of spread relative to the point of entry into the flexible guide tube on the catheter stem, movement of the draw wires can take place with a minimum amount of friction, which guarantees easily movable operation. Only a small amount of control force is required at the control wheel, with the drive pulley-pulling means combination according to the invention.

The guide means can be in the form of a toothed guide pulley which is arranged opposite the toothed drive pulley, the two pulleys jointly with the toothed belt forming a pulling means transmission. It is also possible for the guide means to be in the form of an U-shaped or L-shaped rail which is arranged opposite the toothed drive pulley. Preferably the U-shaped rail can be formed directly by the internal configuration of the gripping element. That situation involves the elimination of separate components for the drive means.

Preferably the entrainment member comprises a fixing portion which correspondingly co-operates in positively locking relationship with the teeth of the toothed belt and which is thus non-displaceable, and an eye portion for a crimp sleeve secured at the end to the draw wire, to permit a pulling movement of the draw wire. The eye portion-crimp sleeve arrangement means that the draw wire can be pulled and prevents the disadvantageous application of a pressure force to the draw wire.

A further feature which improves the invention provides that arranged on the control wheel are friction brake means in order to prevent unwanted resilient return movement of the deflected tip of the catheter. The friction brake means apply a constant frictional force over the entire control movement of the control wheel and thus permit jerk-free fine displacement.

Another improving feature provides that manually variable adjusting means are provided for setting the spacing and the angular position between the gripping portion and a catheter stem. That permits simple adjustment of draw wires, deflection planes and corrugational configuring of the stem.

BRIEF DESCRIPTION OF THE DRAWINGS

Further features for improving the invention are recited in the appendant claims or are set forth in greater detail hereinafter in conjunction with the description of a preferred embodiment of the invention with reference to the drawings in which:

DETAILED DESCRIPTION OF THE PREFERRED EMBODIMENT

Figure 1:
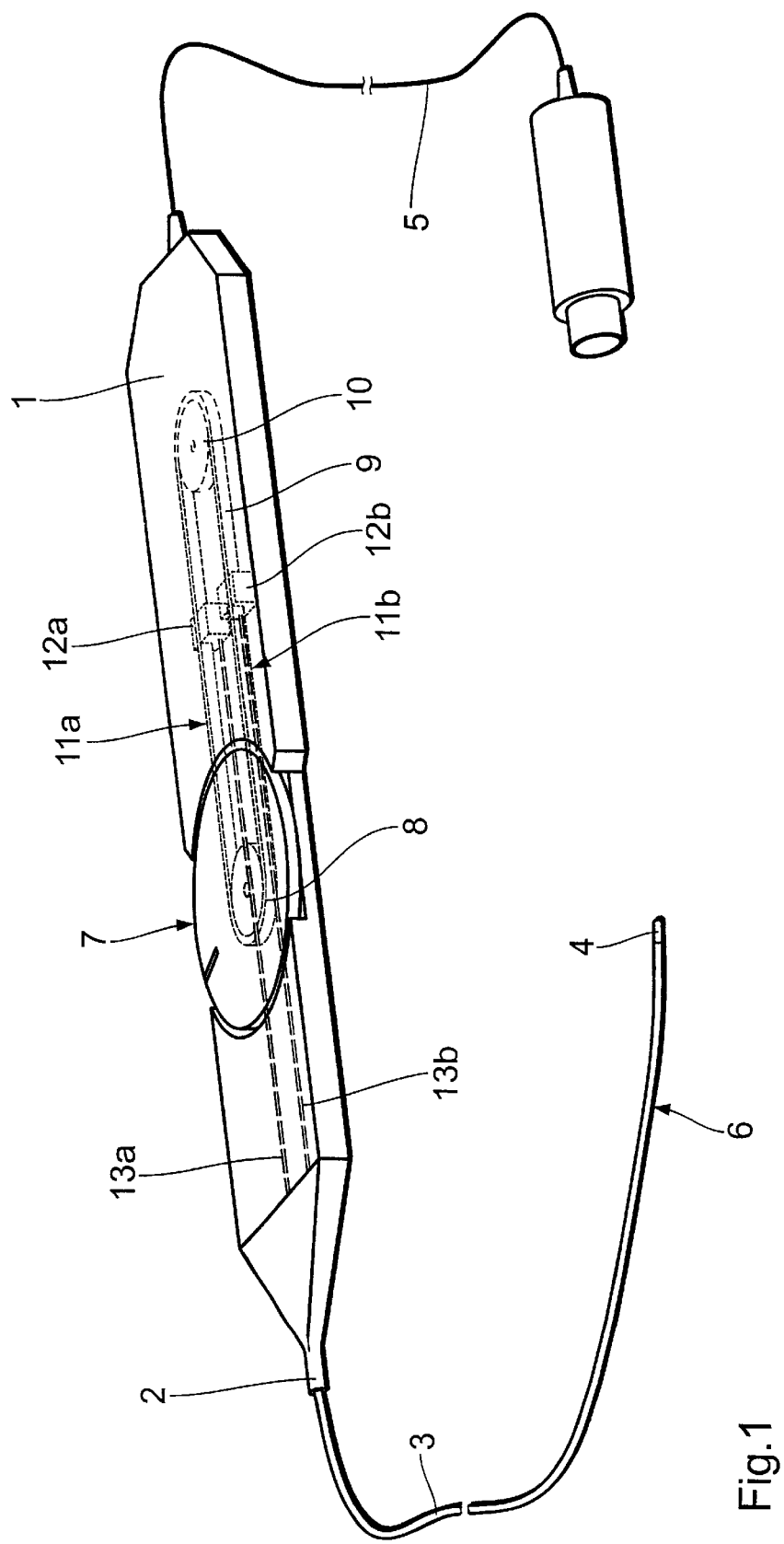
FIG. 1 is an external view of a catheter in the form of an ablation catheter.

The catheter shown in FIG. 1 is in the form of an ablation catheter and comprises a gripping element 1 which goes into a catheter stem 2. Extending from the catheter stem 2 is a flexible guide tube 3 which is introduced from the exterior into the hollow organ which is to be treated in the body. An electrode 4 is arranged at the distal end of the guide tube 3. Besides the electrode 4, sensor means which are not further shown—for example a temperature sensor—may also be provided here, in order to control the success in terms of treatment by means of suitable measurements. The electrical connection to a control unit (also not shown) is made by way of an electric line 5. The control unit serves for evaluation and display of values detected by the sensor means and generates the electromagnetic waves which are outputted by way of the electrode 4 for the ablation of tissue.

The region of the tip 6 of the catheter can be deflected by way of the gripping element 1. The control wheel 7 arranged on the gripping element serves for that purpose. Rotation of the control wheel 7 causes rotation in the same direction of a toothed drive disk or pulley 8 arranged with the control wheel 7 on the same shaft. The toothed drive pulley 8 belongs to a transmission means which are arranged within the gripping element 1 and which are identified by broken lines in the Figure. The transmission means include among the other components described hereinafter in particular a toothed belt 9. The toothed belt 9 has trapezoidal or involute-shaped teeth with which it engages in a play-free fashion into the corresponding teeth on the toothed drive pulley 8. A toothed guide pulley 10 acting as a guide means is rotatably mounted in the gripping element 1 in opposite relationship to the toothed drive pulley 8 in such a way that the toothed belt 9 is under a slight pre-tension which prevents play. The toothed guide pulley 10 also serves for alignment of the toothed belt 9 so that it forms-two straight flank sides 11a and 11b. Entrainment members 12a and 12b are fixed to the flank sides 11a and 11b of the toothed belt 9. The structure of the entrainment members 12a and 12b will be described in greater detail hereinafter. The purpose of the entrainment members 12a and 12b is to transmit a pulling force by way of an eye-crimp sleeve arrangement to draw wires 13a and 13b which are connected to the entrainment members; the transmission of a detrimental pressure force is however prevented. The draw wires 13a and 13b are passed beside electrical cables (not shown here)—which are to be provided at least for the electrode 4—through the catheter stem 2 and the guide tube 3 to the region of the tip 6 of the catheter where the draw wires 13a and 13b are fixed. The draw wires 13a and 13b are coated with PTFE (polytetratfluoroethylene) to minimise friction.

The above-described transmission means convert a rotary control movement which is applied manually to the control wheel 7 into a translatory control movement for the draw wires 13a and 13b which produce a bidirectional delectability of the tip 6 of the cathode, by virtue of a pulling force which can be transmitted alternately. That movement can be combined with a rotary movement about the longitudinal axis of the gripping element 1 so that it is possible to execute deflection in any desired direction and as a result thereof the catheter, by virtue of an additional manual advance movement of the guide tube 3, can follow the desired configuration of a hollow organ in the body.

Figure 2:
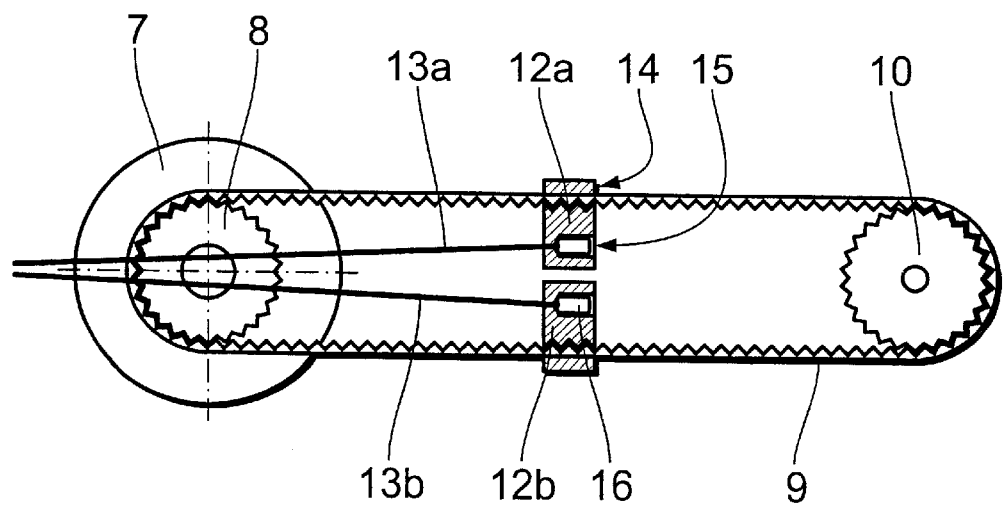
FIG. 2 is a view in principle of transmission means arranged in a gripping element, with the inclusion of a guide roller.

The transmission means which, as shown in FIG. 2, comprise the toothed drive pulley 8 driven by the control wheel 7, the oppositely disposed toothed guide pulley 10, the toothed belt 9 and the two entrainment members 12a, 12b permit straight, low-friction guidance of the draw wires 13a and 13b, with a slight degree of spread thereof. For that purpose, the entrainment members 12a, 12b are arranged to face towards each other. The entrainment member 12a or 12b comprises a fixing portion 14 which co-operates in corresponding positively locking relationship with the teeth of the toothed belt and an eye portion 15 which is in the nature of a reduced through bore. The shoulder in the eye portion 15 serves as an abutment for the associated draw wire 13a or 13b respectively which at its end is provided with a respective crimp sleeve 16 which comes to bear against the shoulder. The eye portion 15 makes it possible to pull the draw wire 13a or 13b respectively. A movement in the opposite direction results in the crimp sleeve 16 sliding out of the eye portion 15.

Figure 3:
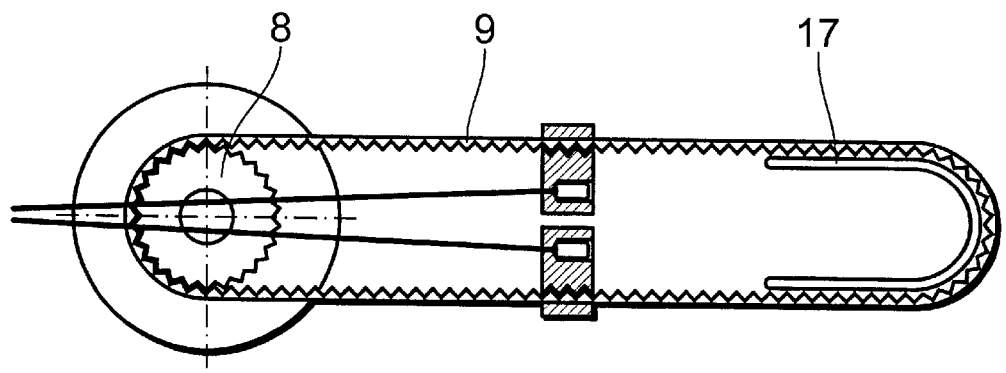
FIG. 3 is a view in principle of transmission means as an alternative to FIG. 2, with a U-shaped rail.

In the embodiment shown in FIG. 3, instead of the toothed guide pulley 10, the guide means used can be in the form of a U-shaped or L-shaped rail 17. The U-shaped or L-shaped rail 17 is directed with its opening towards the toothed drive pulley 8 and is formed by the internal configuration of the gripping element 1. The teeth of the toothed belt 9 slide over the outside surface of the U-shaped rail 17.

Figure 4A:
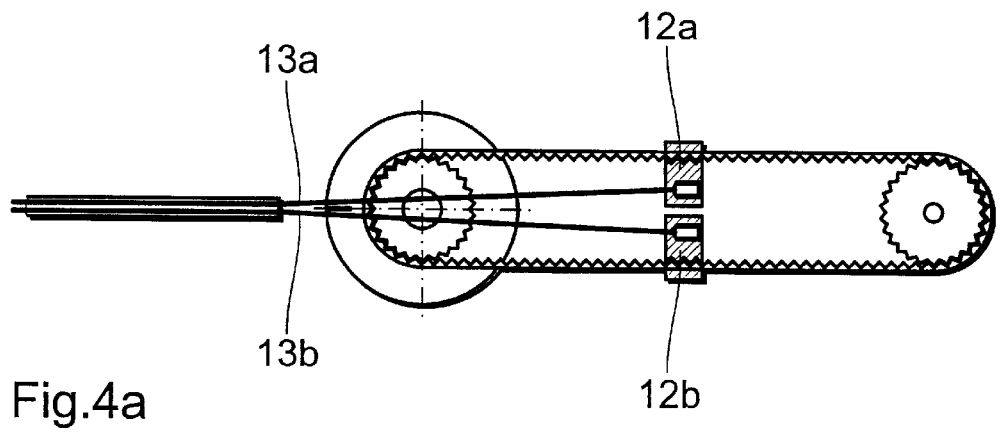
FIGS. 4a through 4c show a sequence of possible positions which the transmission means can adopt in operation.
Figure 4B:
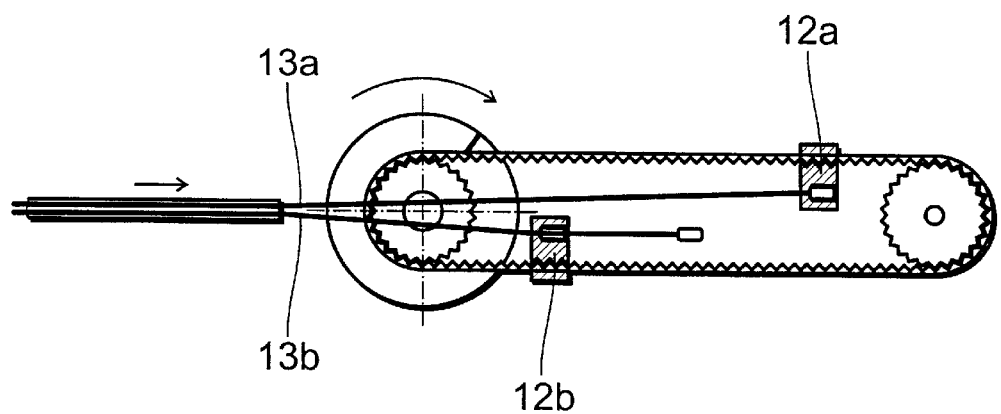
Figure 4C:
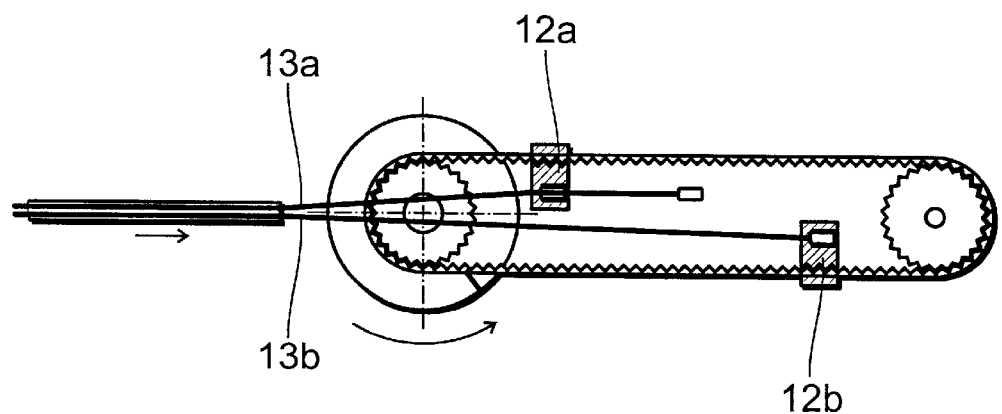

FIG. 4a shows the transmission means of the catheter in the neutral position. The tip 6 of the catheter is then not deflected. The control wheel 7 is in its central position. In that position, the ends of the draw wires 13a and 13b are at approximately the same level and are in a condition of abutment in their respective entrainment members 12a and 12b. FIG. 4b shows a deflection movement which is towards the right, as viewing in the direction of the tip 6 of the catheter. The control wheel 7 is rotated in the clockwise direction. The end of the draw wire 13a is pulled by the entrainment member 12a. The end of the other draw wire 13b is released by the associated entrainment member 12b. FIG. 4c finally shows a deflection movement towards the left, as viewing in the direction of the tip 6 of the catheter. The control wheel 7 is correspondingly rotated in the counterclockwise direction. The end of the draw wire 13b is pulled by the entrainment member 12b. The end of the other draw wire 13a has been released by the associated entrainment member 12a.

Figure 5:
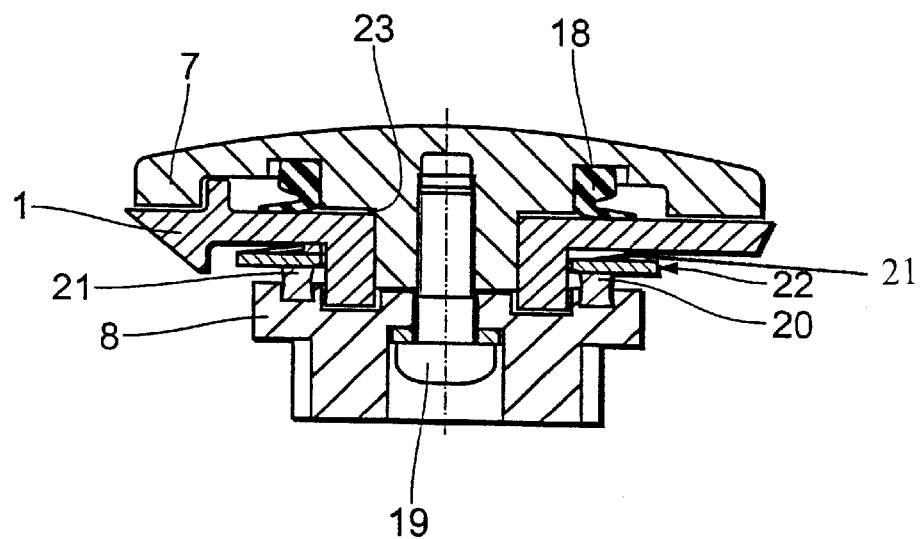
FIG. 5 shows a detail view in section through a control wheel with friction brake means.

FIG. 5 is a detail view in section of the control wheel 7 arranged on the gripping element 1. The control wheel 7 is provided with friction brake means which counteract a tendency to return movement on the part of the deflected tip 6 of the catheter, that is to say the position once set is maintained by the friction brake means. As the control wheel 7 is coupled to the ends of the draw wires 13a and 13b by way of the transmission means as described hereinbefore, the position of the draw wire 13a or 13b which is subjected to a tensile force is therefore maintained in that respect. The arrangement has a sealing ring 18 which is fitted in an opening in the form of an annular groove coaxially in the control wheel 7 and which presses with its sealing lip on the outside against the gripping element 1 and seals off the interior of the gripping element 1 in relation to external environmental influences. The control wheel 7 has a coaxial projection of smaller diameter with which it projects through a through bore in the gripping element 1 and is screwed by means of a screw 19 to the toothed drive pulley 8 in such a way that the control wheel 7 is rotatable with the toothed drive pulley 8 with respect to the gripping element 1. An elastomer ring 20 is disposed on the toothed drive pulley 8 in the interior of the gripping element 1 in an opening in the form of an annular groove in coaxial relationship with the toothed drive pulley 8. An annular pressure plate 22 is disposed in opposite relationship to the elastomer ring 20, as a frictional counterpart. The pressure plate 22 is provided with a PTFE-coating and has a profiled bore. The housing entails an inverse axially extending profile so that rotation of the disk member is prevented, while axial displacement is possible. The plate spring 21 bears against the housing and presses against the pressure plate 22. The plate spring 21 applies a uniform and reproducible normal force for the frictional pairing. The flow of force for the normal force goes from the plate spring 21 which bears against the housing by way of the axially movable pressure plate to the elastomer ring 20 which is connected to the control wheel 7. That frictional pairing between the elastomer ring 20 and the pressure plate 22 minimises what is referred to as the slip-stick effect. An anti-friction ring 23 is provided in the region in which the control wheel 7 is in contact with the gripping element 1, to provide for low-friction fine adjustability. The brake means permit a braking action upon rotation of the control wheel 7 in relation to the gripping element 1.

Figure 6A:
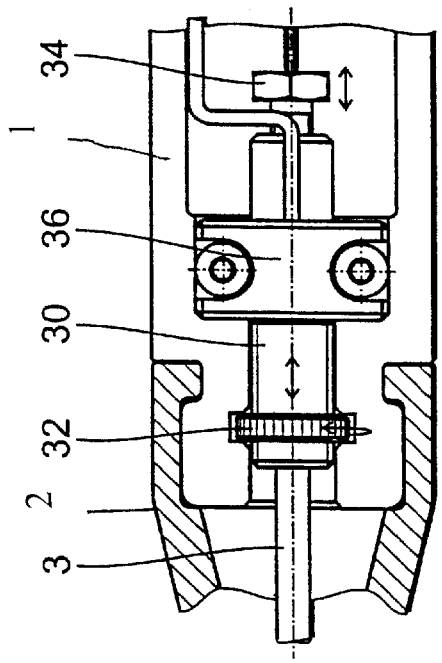
FIGS. 6a and 6b show a detail view in section through adjusting means for positional fixing of components appropriately for the function thereof.
Figure 6B:
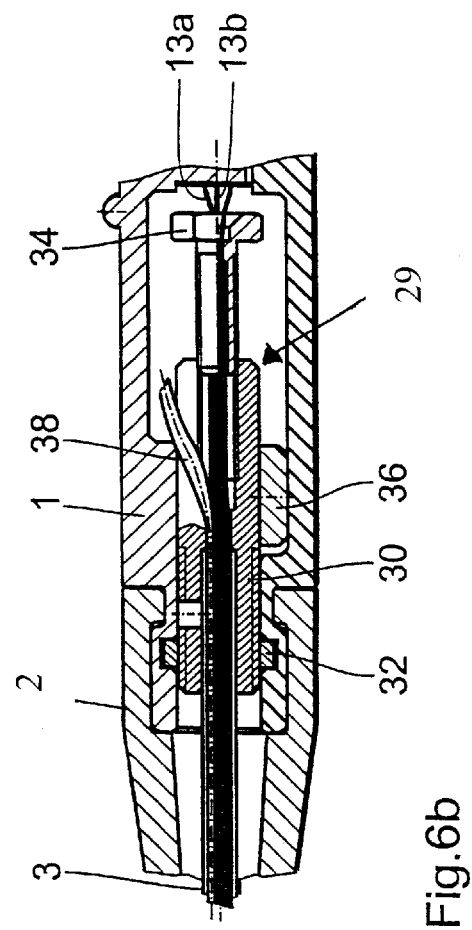

The catheter also has an adjusting mechanism 29 that is shown in FIG. 6 for connecting the catheter stem 2 and the gripping element 1 and for compensating for manufacturing tolerances and for fixing the gripping element 1 in position in relation to the catheter stem 2 appropriately in terms of the function involved. The adjusting means 29 comprise a screwthreaded portion for angular positioning, which is connected stationarily and coaxially to the catheter stem 2 and which is connected to an adjusting nut-adjusting screw arrangement for adjusting the spacing.

The adjusting mechanism 29 includes a screwthreaded sleeve 30, an adjusting nut 32, an adjusting screw 34 and a clamping block 36.

The screwthreaded sleeve 30 is fixedly connected to the flexible guide tube 3 and is fixed by the clamping block 36. In use, the screwthreaded sleeve 30 ensures a fixed connection which however is adjustable upon assembly, between the catheter stem 2 and the gripping element (housing) 1. Radial rotation of the screwthreaded sleeve 30 causes adjustment of the plane of the change in position of the tip of the catheter in relation to the gripping element 1.

The adjusting nut 32 engages with a screwthread into a male screwthread on the adjusting sleeve 30. With the adjusting nut 32, the screwthreaded sleeve 30 can be axially moved with a fine degree of feel and control in the context of the adjustment procedure, while the catheter mechanism is fully operational. That permits exact adjustment and direct monitoring and control thereof. A screwing movement at thie adjusting nut 32 provides for provisional setting as between the catheter stem 2 through flexible guide tube 3 and the adjusting mechanism, that is to say the tensioning of the draw wires 13a and 13b.

The adjusting screw 34 serves to adjust a metal coil or plastic tube which carries pressure forces in the catheter stem 2 and reduces the degree of corrugational distortion of the catheter stem 2 upon deflection.

In addition FIG. 6 also shows an electro-protective feed line 38 which leads for example to electrodes at the distal end of the catheter stem 2.

The invention is not limited in terms of implementation thereof to the preferred embodiment set forth hereinbefore. On the contrary a large number of alternative configurations are possible, which make use of the illustrated structure even in configurations of a basically different kind. In particular the invention also embraces a pulling means which is of a chain-like segmented structure or an arrangement which operates with the involvement of frictional engagement, for the toothed belt 9, within the context of equivalent means. Besides the specific implementation in the form of an ablation catheter, the catheter may also be designed in another fashion, for example as a catheter for introducing medicaments into a hollow organ in the body.

What is claimed is:

1. A bi- or unidirectionally deflectable ablation catheter, comprising:

a gripping element;

a flexible guide tube which extends from the gripping element and which terminates in a catheter tip for treating or investigating a hollow organ in a body, wherein there is at least one draw wire provided for deflection purposes, the at least one draw wire extending within the flexible guide tube and being fixed to the tip of the catheter and being movable by way of a transmission means disposed in the gripping element for converting the rotary movement of a manual control wheel into a longitudinal movement for the draw wire;

wherein a toothed drive pulley which is coupled to the control wheel is provided as the transmission means, the toothed drive pulley correspondingly engaging into the teeth of a toothed belt which is guided over a U-shaped or L-shaped rail that is arranged opposite the toothed drive pulley within the gripping element such that the draw wire is pullingly longitudinally movable by way of an entrainment member fixed to a flank side of the toothed belt.

2. A catheter as set forth in claim 1 characterised in that for a bidirectional deflection precisely two draw wires (13a, 13b) are arranged at both flank sides (11a, 11b) of the toothed belt (9).

3. A catheter as set forth in claim 1 characterised in that the guide means is in the form of a toothed guide pulley (10) which is arranged opposite the toothed drive pulley (8) and which both together with the toothed belt (9) form a pulling means transmission.

4. A catheter as set forth in claim 1 characterised in that the U-shaped or L-shaped rail (17) is formed by the internal configuration of the gripping element (1).

5. A catheter as set forth in claim 1 characterised in that the entrainment member (12a or 12b) comprises a fixing portion (14) which co-operates in correspondingly positively locking relationship with the teeth of the toothed belt (9) and an eye portion (15) for a crimp sleeve (16) which is fixed at the end to the draw wire (13a; 13b), for permitting a pulling movement of the draw wire (13a; 13b).

6. A catheter as set forth in claim 1 characterised in that friction brake means are arranged between the control wheel (7) and the gripping element (1) to avoid an unwanted return movement of the deflected catheter tip (6).

7. A catheter as set forth in claim 6 characterised in that the friction brake means include an elastomer ring (20) which is arranged in coaxial relationship on the inside or the outside on the control wheel (7) or on the drive pulley (8) respectively in an opening in the form of an annular groove, and in opposite relationship with which as a friction counterpart is an annular pressure plate (22), wherein a plate spring (21) which is fixed to the gripping element (1) applies a normal force to the pressure plate (22).

8. A catheter as set forth in claim 7 characterised in that the annular pressure plate (22) is provided with a PTFE-coating.

9. A catheter as set forth in claim 1 characterised in that there are provided manually settable adjusting means for setting the spacing and for varying the angular position as between the gripping element (1) and a catheter stem (2).

10. A catheter as set forth in claim 9 characterised in that the adjusting means comprise a screwthreaded portion for the angular position which is stationarily and coaxially connected to the catheter stem (2) and which is connected to an adjusting nut-adjusting screw arrangement for adjusting the spacing.

11. A catheter as set forth in claim 1 characterised in that the catheter as an ablation catheter is equipped at the tip (6) of the catheter with an electrode (4) which is fed by way of an electric line (5) at the end of the gripping element (1), which is opposite to the flexible guide tube (3).

12. A catheter as set forth in claim 11 characterised in that besides the electrode (4) the tip (6) of the catheter is also provided with sensor means for monitoring/controlling the treatment.

13. A bi- or unidirectionally deflectable ablation catheter, comprising:

a gripping element;

a flexible guide tube which extends from the gripping element and which terminates in a catheter tip for treating or investigating a hollow organ in a body;

wherein there is at least one draw wire provided for deflection purposes, the at least one draw wire extending within the flexible guide tube and being fixed to the tip of the catheter and being movable by way of a transmission means disposed in the gripping element for converting the rotary movement of a manual control wheel into a longitudinal movement for the draw wire;

wherein a toothed drive pulley which is coupled to the control wheel is provided as the transmission means, the toothed drive pulley correspondingly engaging into the teeth of a toothed belt which is guided over a guide means within the gripping element such that the draw wire is pullingly longitudinally movable by way of an entrainment member fixed to a flank side of the toothed belt; and wherein a friction brake means is arranged between the control wheel and the gripping element to avoid an unwanted return movement of the deflected catheter tip, the friction brake means including an elastomer ring which is arranged in coaxial relationship on the inside or the outside on the control wheel or on the drive pulley respectively in an opening in the form of an annular groove, and in opposite relationship with which as a friction counterpart is an annular pressure plate, provided with a PTFE-coating, wherein a plate spring which is fixed to the gripping element applies a normal force to the pressure plate.

14. A catheter as set forth in claim 13 characterised in that for a bidirectional deflection precisely two draw wires (13a, 13b) are arranged at both flank sides (11a, 11b) of the toothed belt (9).

15. A catheter as set forth in claim 13 characterised in that the guide means is in the form of a toothed guide pulley (10) which is arranged opposite the toothed drive pulley (8) and which both together with the toothed belt (9) form a pulling means transmission.

16. A catheter as set forth in claim 13 characterised in that the entrainment member (12a or 12b) comprises a fixing portion (14) which co-operates in correspondingly positively locking relationship with the teeth of the toothed belt (9) and an eye portion (15) for a crimp sleeve (16) which is fixed at the end to the draw wire (13*a*; 13*b*), for permitting a pulling movement of the draw wire (13*a*; 13*b*).

17. A catheter as set forth in claim 13 characterised in that there are provided manually settable adjusting means for setting the spacing and for varying the angular position as between the gripping element (1) and a catheter stem (2).

18. A catheter as set forth in claim 17 characterised in that the adjusting means comprise a screwthreaded portion for the angular position which is stationarily and coaxially connected to the catheter stem (2) and which is connected to an adjusting nut-adjusting screw arrangement for adjusting the spacing.

19. A catheter as set forth in claim 13 characterised in that the catheter as an ablation catheter is equipped at the tip (6) of the catheter with an electrode (4) which is fed by way of an electric line (5) at the end of the gripping element (1), which is opposite to the flexible guide tube (3).

20. A catheter as set forth in claim 19 characterised in that besides the electrode (4) the tip (6) of the catheter is also provided with sensor means for monitoring/controlling the treatment.

\* \* \* \* \*